(12) United States Patent
Yamada et al.

(10) Patent No.: US 6,242,429 B1
(45) Date of Patent: Jun. 5, 2001

(54) ARABINOSYLADENINE DERIVATIVES

(75) Inventors: Toshio Yamada, Ono; Koichi Yamanishi, Osaka, both of (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/339,257

(22) Filed: Jun. 24, 1999

(30) Foreign Application Priority Data

Jun. 24, 1998 (JP) .................................. 10-177209

(51) Int. Cl.$^7$ .......................... A61K 31/70; A01N 43/04

(52) U.S. Cl. .............................. 514/46; 514/45; 514/47; 514/934; 536/27.4

(58) Field of Search ................. 514/45, 46, 47, 514/934; 536/27.4

(56) References Cited

U.S. PATENT DOCUMENTS

| | | |
|---|---|---|
| 4,843,066 | 6/1989 | Yamada et al. . |
| 4,985,409 | 1/1991 | Yamada et al. . |
| 5,424,295 | 6/1995 | Krenitsky et al. . |
| 5,539,098 | 7/1996 | Krenitsky et al. . |
| 5,705,491 | * 1/1998 | Yamada .................................. 514/46 |
| 5,773,603 | 6/1998 | Yamada . |

FOREIGN PATENT DOCUMENTS

| | | |
|---|---|---|
| 0 181 129 A3 | 5/1986 | (EP) . |
| 0 219 876 A2 | 4/1987 | (EP) . |
| 0286028 | * 10/1987 | (EP) .................................. 536/27.4 |
| 0 269 574 A2 | 6/1988 | (EP) . |
| 0 378 518 A2 | 7/1990 | (EP) . |
| 0 490 818 A1 | 6/1992 | (EP) . |
| 2 226 027 | 6/1990 | (GB) . |
| 55-45625 | 3/1980 | (JP) . |
| 63-239294 | 10/1988 | (JP) . |
| 63-310831 | 12/1988 | (JP) . |
| 2-184696 | 7/1990 | (JP) . |
| 2-218689 | 8/1990 | (JP) . |
| WO 88/03147 | 5/1988 | (WO) . |
| WO 92/05177 | 4/1992 | (WO) . |

OTHER PUBLICATIONS

Sloan, B., et al., *Ann. N.Y. Acad. Sci.*, vol. 284, pp. 60–80 (1977).
Kotra, L.P., et al., *J. Med. Chem.*, vol. 39, pp. 5202–5207 (1996).
Koszalka, G.W., et al., *Antimicrobial Agents and Chemotherapy*, vol. 35, pp. 1437–1443 (1991).
Averett, D.R., et al., *Antimicrobial Agents and Chemotherapy*, vol. 35, pp. 851–857 (1991).
Sato et al., *Chem. Pharm. Bull.*, vol. 37, pp. 1604–1608 (1989).
Mitsunobu, O., *Synthesis*, p. 1, 1981.
Nair, V. et al., *Synthesis*, pp. 670–672 (1982).
Ueeda, M., et al., *J. Med. Chem.*, vol. 34, pp. 1334–1339 (1991).
J.G. Niedzwicki, et al, "Structure–Activity Relationship of Ligands of Human Plasma Adenosine Deaminase$_2$", *Biochemical Pharmacology*, vol. 41, No. 11, 1991, pp. 1615–1624.
The 1991 Sigma Chemical Company Catalog, St. Louis, MO, pp. 41 and 660.
Phillis, et al., "Brain Adenosine and Transmitter Amino Acid Release from the Ischemic Rat Cerebral Cortex: Effects of the Adenosine Deaminase Inhibitor Deoxycoformycin", *Journal of Neurochemistry*, vol 56, No. 2, pp. 644–650 (1991).
Cristalli, et al., "Adenosine Deaminase Inhibitors: Synthesis and Structure–Activity Relationships of 2–Hydroxy–3–nonyl Derivatives of Azoles", *J. Med. Chem.*, vol. 37, pp. 201–205 (1994).
Zhu, et al., "Protective effects of an adenosine deaminase inhibitor on ischemia–reperfusion injury in isolated perfused rat heart", *Am. J. Physiol.*, vol. 259, H835–H838 (1990).
Kato, et al., "Effects of Antiasthma Drugs on Superoxide Anion Generation from Human Polymorphonuclear Leukocytes or Hypoxanthine–Xanthine Oxidase System", *Int. Arch. Allergy Appl. Immunol.*, vol. 96, pp. 128–133 (1991).
Rockwell et al., "Studies on Adenosine Deaminase I. Purification and Properties of Ox Hear Adenosine Deaminase," *Mol. Pharmacol.* 2, 574–584 (1966).

(List continued on next page.)

*Primary Examiner*—James O. Wilson
(74) *Attorney, Agent, or Firm*—Hollander Law Firm, P.L.C (57) ABSTRACT

Antiviral Ara-A derivatives having resistance to metabolism by adenosinedeaminase (ADA) are 2-substituted arabinosyladenine derivatives represented by the formula (I) and pharmaceutically acceptable salts and hydrates thereof:

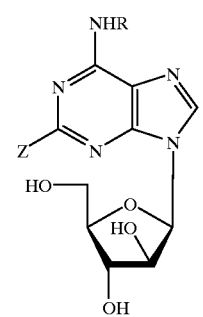

[I]

wherein Z is alkyl having at least 4 carbon atoms, alkenyl or alkynyl and R is hydrogen or lower alkyl. The compounds are useful as therapeutic or preventive agents for diseases infected by DNA virus such as herpes simplex virus (HSV), herpes zoster virus, cytomegalovirus (CMV), adenovirus, hepatitis virus or vaccinia virus. As compared with Ara-A, they not only show good activity in blood with an excellent sustaining property but also are capable of being orally administered without substantial loss of pharmaceutical effectiveness due to metabolism by ADA.

19 Claims, 3 Drawing Sheets

OTHER PUBLICATIONS

Richard, et al., "Open clinical study of liposomal superoxide dismutase in severe rheumatoid arthritis. Study of a series of 7 cases." *Therapie* (France), Jul.–Aug. 1989, 44(4), pp. 291–295.

Dejica, et al., "Local treatment with Epurox (superoxide dismutase and catalase of human origin) in the chronic inflammatory and degenerative rheumatism", *Arch. Roum. Pathol Exp. Microbiol.* (Romania), Jul.–Dec. 1986, 45(3–4), pp. 299–310.

Corvetta, et al., "Rifamycin and superoxide dismutase in the treatmen of rheumatoid synovitis of the knee", *Recenti Prog. Med.* (Italy), May 1985, 76(5), pp. 265–268.

Pasquier, et al., "Superoxide dismutases in polymorphonuclear leukocytes from patients with ankylosing spondylitis or rheumatoid arthritis", *Clin. Exp. Rheumatol.* (Italy), Apr.–Jun. 1985, 3(2), pp. 123–126.

Camus, et al., "Superoxide dismutase and rheumatoid arthritis. Study of a series of 6 cases.", *Rev. Rhum. Mal. Osteoartic* (France), Jul.–Sep. 1980, 47(7–9), pp. 489–492.

The Merck Index, Tenth Edition, 1983, pp. 762–763.

Martin et al., *Arzneim–Forsch/Drug Res.*28(I) Heft 5, pp. 770–782, 1978.

Greene, T.W., *Protective Groups in Organic Synthesis*, John Wiley & Sons, Inc., 1981.

Kharasch et al., "The Addition of Hydrogen Halides to cis– and trans–2–Pentene," *J. Am. Chem. Soc.*, vol. 61, pp. 1559–1564 (1939).

Campbell et al., "The Preparation of Higher cis and trans Olefins," *J. Am. Chem. Soc.*, vol. 63, pp. 216–219 (1941).

Hatch et al., "Allylic Chlorides. IX. Preparation of cis and trans Crotyl Chloride," *J. Am. Chem. Soc.*, vol. 72, pp. 727–730 (1950).

Taira, "Reduction of Organic Compounds with Urushibara Catalysts under High Pressure. X. Hydrogenation of 2–Butyne–1,4–diol to cis–2–Butene–1,4–diol with various Urushibara Catalysts," *Bull. Chem. Soc Jpn.*, vol. 35, pp. 840–844 (1962).

Cram et al., "Macro Rings. XIII. Synthesis and Properties of 1,7–Cyclododecadiyne and Related Compounds," *J. Am. Chem. Soc.*, vol. 78, pp. 2518–2524 (1956.

\* cited by examiner

ARABINOSYLADENINE DERIVATIVES

FIELD OF THE INVENTION

The present invention relates to 2-substituted arabinosyladenine derivatives having resistance to metabolism by adenosinedeaminase, pharmaceutical compositions containing the derivatives, and their use as an antiviral agent.

BACKGROUND OF THE INVENTION

Arabinosyladenine (general name: vidarabine; hereinafter referred to as "Ara-A") is effective against DNA viruses such as herpes simplex virus (HSV), herpes zoster virus, cytomegalovirus (CMV), adenovirus, hepatitis virus and vaccinia virus. Clinically, it is mainly used as a therapeutic agent for infectious diseases associated with or caused by herpes virus. However, Ara-A is quickly metabolized by adenosinedeaminase (ADA) in the blood stream to hypoxanthine arabinoside which has weak antiviral activity. Therefore, a disadvantage of Ara-A is that its strong antiviral activity in vitro is not reflected in clinical efficacy. In addition, ADA is abundantly present in the digestive tract and, therefore, orally administered Ara-A is metabolized before being absorbed. Accordingly, oral administration of Ara-A is very difficult and, at present, only Ara-A ointment and Ara-A injections have been commercially available.

Until now, various attempts have been made for stabilization of Ara-A but each of them has the following problems and is not satisfactory:

(1) A method using Ara-A and an ADA inhibitor jointly [Sloan, B., et al, *Ann. NY. Acad. Sci.*, vol. 284, pages 60–80 (1977)].

Sloan et al discloses a method where Ara-A and an ADA inhibitor are simultaneously administered in order to stabilize Ara-A. Deoxycoformycin was used as an ADA inhibitor but an adverse reaction due to the combination was observed whereby the development was abandoned.

(2) A method for making a prodrug of Ara-A [Kotra, L. P., et al, *J. Med. Chem.*, vol. 39, pages 5202–5207 (1996)].

Kotra et al discloses a method where a compound in which an amino group at the 6-position of Ara-A is substituted with an azide group is used as a prodrug. This azide group is reduced to an amino group by cytochrome P-450 in a hepatic microsome fraction to give Ara-A in vivo. However, it is presumed that, even as compared with this reduction reaction, the metabolism by ADA is far quicker whereby it is hardly believed that the concentration of Ara-A in blood increases. Actually, although the authors describe the behavior in blood of the prodrug, 6-azido-Ara-A, they do not mention at all whether the active Ara-A itself was present in blood.

(3) A method using Ara-A derivatives resistant to metabolism by ADA [Koszalka, G. W., et al, *Antimicrobial Agents and Chemotherapy*, vol. 35, pages 1437–1443 (1991); Averett, D. R., et al, *Antimicrobial Agents and Chemotherapy*, vol. 35, pages 851–857 (1991)].

Syntheses of Ara-A analogs resistant to metabolism by ADA have been frequently conducted. Koszalka et al introduced a methylamino group, dimethylamino group or methoxyl group into the 6-position of the base and synthesized Ara-A analogs having a resistance to metabolism by ADA. This is also mentioned in Japanese Laid-Open Patent Publication Sho-63/310831. However, those compounds did not show sufficient resistance to ADA. According to a study by the present inventors, the compound of Koszalka et al (6-methylamino-9-(β-D-arabinofuranosyl)purine which is control compound C in Comparative Example 2 below and in FIG. 3) wherein a methylamino group is present in the 6-position, showed insufficient resistance to ADA. The resistance of the compound containing an introduced methoxyl group was weak as well. The compound which contains the dimethylamino group at the 6-position showed resistance to ADA. However, the compound is easily demethylated to a monomethyl compound in vivo and, as a result, it is also metabolized by ADA.

Figure 1:
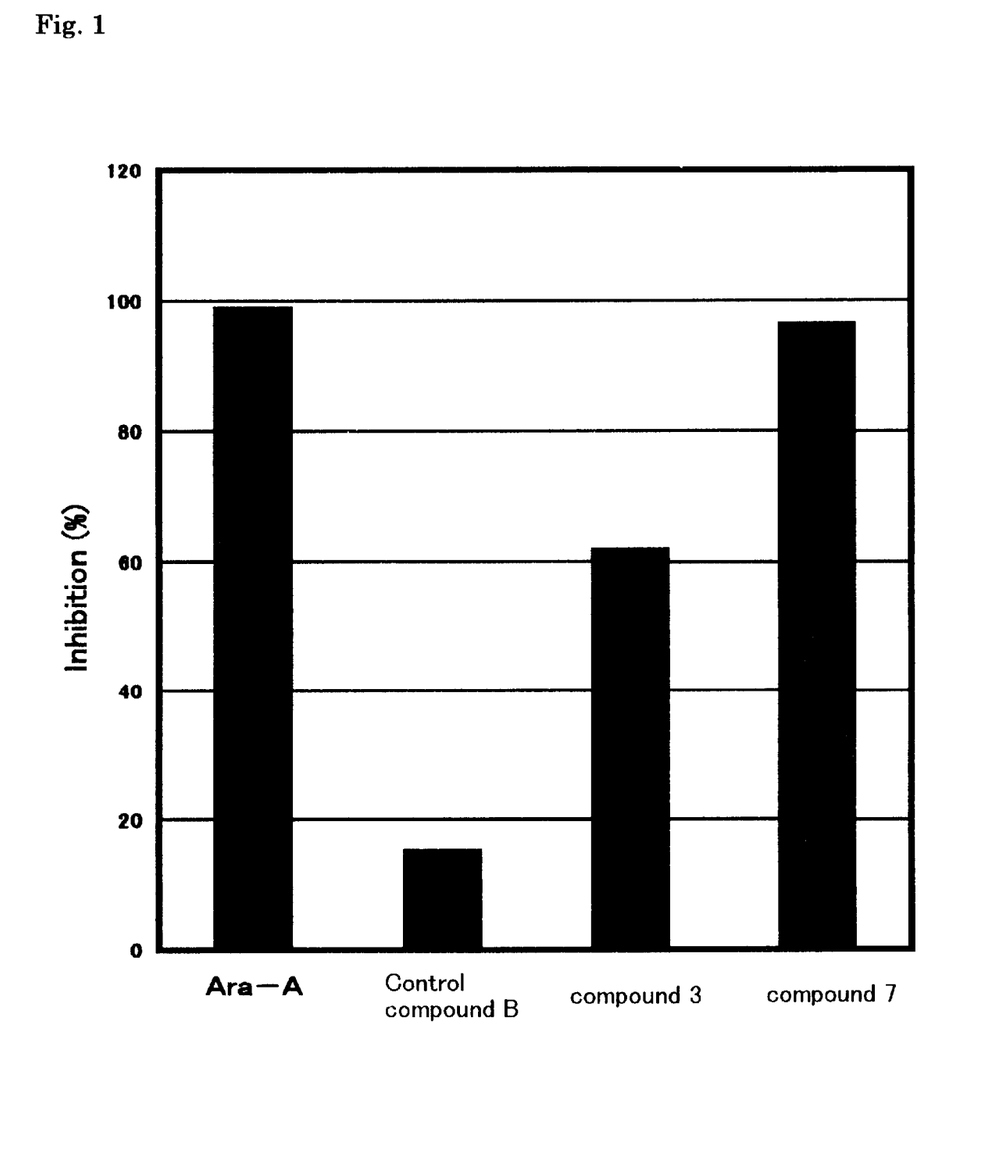
FIG. 1 is an example of results showing the inhibitory activity of the compounds of the present invention against herpes zoster virus.

With regard to 2-alkyl derivatives of Ara-A, a compound where a methyl group is introduced into the 2-position (9-(β-D-arabinofuranosyl)-2-methyladenine which is control compound A in Comparative Example 1 below) is disclosed in Japanese Laid-Open Patent Publication Sho-55/45625. A compound where an ethyl group is introduced into the 2-position (9-(β-D-arabinofuranosyl)-2-ethyladenine which is control compound B in Comparative Example 1 below and in FIG. 1) is described in Keiko Sato et al, *Chem. Pharm. Bull.*, vol. 37, pages 1604–1608 (1989). As a result of testing by the present inventors, no strong antiviral action is obtained as shown in FIG. 1 even when a lower alkyl group such as methyl or ethyl is introduced into the 2-position of Ara-A. In addition, those compounds are not satisfactory in terms of resistance to ADA.

The present invention solves the above-mentioned problems and provides Ara-A derivatives having resistance to metabolism by ADA and having substantial antiviral action.

SUMMARY OF THE INVENTION

The present inventors have carried out an intensive investigation for Ara-A derivatives having a high resistance to ADA and found novel 2-substituted Ara-A derivatives which exhibit substantial antiviral activity and unexpectedly superior resistance to metabolism by adenosinedeaminase (ADA). The compounds of the present invention, unlike Ara-A, provide high resistance to metabolism by ADA, without deterioration of the antiviral action of Ara-A. Accordingly, the compounds of the present invention not only show good behavior in blood with an excellent sustaining property as good as Ara-A but also are capable of being administered as an oral agent. Therefore, the compounds of the present invention have very high usefulness as therapeutic or preventive agents for diseases infected by DNA virus such as herpes simplex virus (HSV), herpes zoster virus, cytomegalovirus (CMV), adenovirus, hepatitis virus or vaccinia virus.

DETAILED DESCRIPTION OF THE INVENTION

The present invention provides a 2-substituted arabinosyladenine derivative represented by formula (I) and pharmaceutically acceptable salts and hydrates thereof. Furthermore, the present invention relates to an antiviral agent containing said compounds as an effective component. The 2-substituted arabinosyladenine derivatives of formula (I) are:

[I]

In the formula, Z is alkyl having four or more carbon atoms, preferably a linear or branched alkyl having 4 to 12 carbon atoms such as butyl, isobutyl, sec-butyl, tert-butyl, pentyl, isopentyl, neopentyl, hexyl, dimethylbutyl, heptyl, octyl, nonyl, decyl, undecyl or dodecyl; alkenyl, preferably a linear or branched alkenyl having 2 to 12 carbon atoms such as vinyl, propenyl, butenyl, pentenyl, hexenyl, heptenyl, octenyl, nonenyl, decenyl, undecenyl or dodecenyl; or alkynyl, preferably a linear or branched alkynyl having 2 to 12 carbon atoms such as ethynyl, propynyl, butynyl, pentynyl, hexynyl, heptynyl, octynyl, nonynyl, decynyl, undecynyl or dodecynyl. R is hydrogen or lower alkyl, preferably a linear or branched alkyl having 1 to 4 carbon atoms such as methyl, ethyl, propyl, isopropyl, butyl, isobutyl, sec-butyl or tert-butyl.

Preferred embodiments of the present invention are:

(1) A 2-substituted arabinosyladenine derivative represented by the above formula (I) and pharmaceutically acceptable salts and hydrates thereof.

(2) A 2-substituted arabinosyladenine derivative according to paragraph (1) wherein Z is alkyl having four or more than 4 carbon atoms, alkenyl having four or more than 4 carbon atoms or alkynyl having four or more than 4 carbon atoms.

(3) A 2-substituted arabinosyladenine derivative according to paragraph (1) or (2) wherein Z is alkyl or alkynyl.

(4) A 2-substituted arabinosyladenine derivative according to paragraph (3) wherein Z is alkyl.

(5) A 2-substituted arabinosyladenine derivative according to paragraph (4) wherein Z is alkyl having 4 to 12 carbon atoms.

(6) A 2-substituted arabinosyladenine derivative according to paragraph (5) wherein R is hydrogen.

(7) A 2-substituted arabinosyladenine derivative according to paragraph (5) wherein R is alkyl.

(8) A 2-substituted arabinosyladenine derivative according to paragraph (7) wherein R is alkyl having 1 to 4 carbon atoms.

(9) A 2-substituted arabinosyladenine derivative according to paragraph (3) wherein Z is alkynyl.

(10) A 2-substituted arabinosyladenine derivative according to paragraph (9) wherein Z is alkynyl having 4 to 12 carbon atoms.

(11) A 2-substituted arabinosyladenine derivative according to paragraph (10) wherein R is hydrogen.

(12) A 2-substituted arabinosyladenine derivative according to paragraph (10) wherein R is alkyl.

(13) A 2-substituted arabinosyladenine derivative according to paragraph (12) wherein R is alkyl having 1 to 4 carbon atoms.

(14) An antiviral agent containing a 2-substituted arabinosyladenine derivative according to any of paragraphs (1) to (13) as an effective component.

(15) An antiviral agent according to paragraph (14) which has a resistance to metabolism by adenosinedeaminase.

(16) An antiviral agent according to paragraph (14) or (15) which is a preparation for oral administration.

The above-mentioned novel Ara-A derivatives of the present invention may be manufactured by using the following exemplary methods:

Manufacturing Method No. 1

When 5-amino-1-(β-D-arabinofuranosyl)-4-cyanoimidazole (AICN arabinoside) represented by the following formula [II] is made to react with a nitrile represented by the following formula [III], a 2-substituted Ara-A derivative represented by the above formula [I] in which R is hydrogen is obtained:

[II]

Z—CN    [III]

wherein in formula III, Z is the same as that of formula (I).

Reaction of the compound represented by formula [II] with the compound represented by formula [III] is usually carried out using from one to an excessive molar or, preferably, 1–5 mole(s) of the compound represented by the formula [III] to one mole of the compound represented by the formula [II]. Usually, a solvent saturated with ammonia gas is used in the reaction. Examples of the solvent for the reaction are an alcohol such as methanol and ethanol; a halogenated hydrocarbon such as methylene chloride, chloroform, carbon tetrachloride, dichloroethane and trichloroethane; an ether such as ethyl ether, tetrahydrofuran and dioxane; an aromatic hydrocarbon such as benzene, toluene and xylene; an aprotic polar solvent such as dimethylformamide, acetonitrile and ethyl acetate; and a mixed solvent thereof and, among them, the use of alcohol is preferred. Reaction temperature is usually from room temperature to 200° C. or, preferably, from 150° C. to 200° C. Reaction time is usually from one hour to five days or, preferably, from 1 to 24 hours.

Manufacturing Method No. 2

When a compound represented by the following formula [IV]

[IV]

wherein R is the same as that of formula (I) and X is halogen, is made to react with an alkyne represented by the following formula [V],

R'—C≡CH                                    [V]

wherein, R' is alkyl, a 2-substituted Ara-A derivative represented by the above formula [I] where Z is an alkynyl group is obtained. In that case, an alkynyl group is introduced into the 2-position and it can be reduced by conventional methods to give an alkyl group or an alkenyl group.

The reaction of the compound represented by the formula [IV] with the compound represented by the formula [V] is carried out using one or more moles, preferably 1.2 moles, of the compound represented by formula [V] to one mole of the compound represented by formula [IV]. The reaction may be conducted by adding 0.01–1 mole or preferably 0.1 mole of bistriphenylphosphine palladium (II), 0.5–2 mole(s) or preferably 0.5 mole of cuprous iodide and 1–5 mole(s) or preferably 1.2 moles of triethylamine to one mole of the compound represented by the formula [IV]. In conducting this reaction, it is preferred that X in the compound represented by the formula [IV] is an iodine atom. Examples of the solvent for the reaction are an alcohol such as methanol or ethanol; a halogenated hydrocarbon such as methylene chloride, chloroform, carbon tetrachloride, dichloroethane or trichloroethane; an ether such as ethyl ether, tetrahydrofuran or dioxane; an aromatic hydrocarbon such as benzene, toluene or xylene; an aprotic polar solvent such as dimethylformamide, acetonitrile or ethyl acetate; and a mixed solvent thereof and, among them, the use of an alcohol is preferred. The reaction temperature is usually from room temperature to 150° C. or, preferably, from 50° C. to 100° C. Reaction time is usually from 1 hour to 8 hours or, preferably, from 1 hour to 5 hours.

Reduction of the 2-alkynyl derivative may be carried out by an alkali metal such as sodium or lithium or by means of a catalytic reduction using palladium carbon or Raney nickel although the use of palladium carbon is preferred.

Manufacturing Method No. 3

The hydroxyl groups at the 3- and 5-positions of a sugar moiety of a 2-substituted adenosine derivative represented by the following formula [VI]

[VI]

wherein Z and R are the same as those of the formula (I), may be appropriately protected and then a steric rearrangement reaction may be carried out for the 2-position of the sugar moiety followed by removing said protective group after the reaction whereupon a 2-substituted Ara-A derivative represented by the above formula [I] is obtained.

Examples of the protective group which may be employed are a lower alkylsilyl group such as trimethylsilyl, tert-butylsilyl and tetraisopropyldisiloxyl; a lower alkoxymethyl group such as methoxymethyl and methoxyethoxymethyl; and an aralkyl group such as trityl and, among them, a tetraisopropyldisiloxyl group is particularly preferred.

The rearrangement reaction at the 2-position may be carried out by: 1) a method where an alkylsulfonyl group such as a trifluoromethanesulfonyl group, a tosyl group or a mesyl group or an arylsulfonyl group is introduced as a leaving group followed by hydrolyzing, 2) a method where a DMSO oxidation using dicyclohexylcarbodiimide and acetic anhydride as activators is employed followed by reducing with sodium borohydride, or 3) a Mitsunobu reaction [Mitsunobu, O., *Synthesis,* page 1 (1981)], etc.

Removal of the leaving group may vary depending upon its type and may be carried out by a method of Green, T. W., *Protective Groups in Organic Synthesis,* John Wiley & Sons (1981) or a method similar thereto.

The compounds represented by the formulae [II], [III], [V], [VI] and [VII] used as the starting materials in the above manufacturing methods are commercially available or may be synthesized by a method mentioned in the literature, or by a method similar thereto. The compounds represented by the formulae [II] and [III] are mentioned, for example, in Sato, U. et al, *Chem. Pharm. Bull.,* vol. 37, pages 1604–1608 (1989) and Ueeda, M. et al, *J. Med. Chem.,* vol. 34, pages 1334–1339 (1991), respectively. The compound represented by the formula [IV] may be manufactured by a method where hydroxyl groups at the 3- and 5-positions of the sugar moiety of 2-iodoadenosine [Nair, V., et al, *Synthesis* pages 670–672 (1982)] are appropriately protected in the above-mentioned manner, a steric rearrangement reaction for the 2-position is conducted and, after the reaction, said protective group is removed.

The compound of formula [I] obtained by the above manufacturing methods 1–3 is isolated and purified by applying conventional separating means such as column chromatography using silica gel or adsorptive resin, liquid chromatography, solvent extraction, recrystallization or reprecipitation, either solely or jointly. The compounds may be identified by means of, for example, elementary analysis, melting point measurement, infrared (IR), nuclear magnetic resonance (NMR), ultraviolet (UV), and mass spectroscopy (MS).

The compounds represented by the above-given formula (I) include the pharmaceutically acceptable salts thereof such as acid addition salts with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid or sulfanilic acid; salts with an alkali metal such as sodium or potassium, salts with an alkaline-earth metal such as calcium or magnesium, and salts with other metals such as aluminum; or salts with bases such as ammonia or organic amines. Those salts may be manufactured by known methods from the compounds of the present invention in a free state or may be mutually converted among the salts.

When there are steric isomers such as a cis-trans isomer, optical isomer, or a conformational isomer and a hydrate for the substances of the present invention, the present invention includes any and all of them.

The compounds of the present invention, which include the 2-substituted arabinosyladenine derivatives represented by the formula (1) and pharmaceutically acceptable salts and hydrates thereof, can be made into pharmaceutical preparations by combining one or more of the compounds with at least one pharmaceutically acceptable carrier or diluent. Any of the known methods for providing preparations, such as for oral or parenteral administrations (e.g. solids, semisolids, liquids, or gases) may be used to produce the pharmaceutical compositions of the present invention. For example, for oral administrations tablets, capsules, powders, liquids, etc. may be employed. Parenteral administrations may be subcutaneous, intravenous, intramuscular, intrarectal and intranasal administrations. In preparing the preparations, the 2-substituted arabinosyladenine derivatives of the present invention may be used in the form of their pharmaceutically acceptable salts. The compounds of the present invention may be used either solely or jointly in pharmaceutically effective amounts for treating animals or humans. The compounds of the invention can be used either solely or jointly together in pharmaceutically acceptable amounts with pharmaceutically effective amounts of other pharmaceutically active components in pharmaceutical compositions or preparations.

The compounds of the present invention can be used as therapeutic or preventive agents for diseases infected by DNA virus such as herpes simplex virus (HSV), herpes zoster virus, cytomegalovirus (CMV), adenovirus, hepatitis virus or vaccinia virus, by formulating them into a suitable preparation for the administration which may be oral, rectal, nasal, local (including intraoral and sublingual), vaginal or parenteral (including subcutaneous, intramuscular, intracutaneous, intravenous, subarachnoidal and intradural).

In the case of preparations for oral administration, one or more of the compounds of the present invention either alone or in combination with commonly-used pharmaceutically acceptable excipients in pharmaceutically acceptable amounts such as at least one suitable pharmaceutically acceptable additive or carrier (e.g. lactose, mannitol, corn starch, potato starch, potassium citrate, etc.) may be mixed with one or more pharmaceutically acceptable: (1) binders such as cellulose derivatives (e.g. crystalline cellulose, cellulose, hydroxypropylcellulose, etc.), gum arabicum, corn starch, gelatin, etc., (2) disintegrating agents such as corn starch, potato starch, potassium carboxymethylcellulose, calcium carboxymethylcellulose, etc., (3) lubricating agents such as talc, magnesium stearate, etc. and (4) other pharmaceutically acceptable excipients including pharmaceutically acceptable bulking agents, moisturizing agents, buffers, preservatives, perfumes and the like to obtain tablets, diluted powders, granules or capsules.

Alternatively, suppositories may be prepared by mixing at least one compound of the present invention with pharmaceutically acceptable amounts of one or more pharmaceutically acceptable fatty/oily bases (e.g. cacao butter), emulsified bases, water-soluble bases (e.g. Macrogol), hydrophilic bases, etc.

In the case of injections, it is possible to prepare solutions or suspensions of one or more compounds of the present invention in pharmaceutically acceptable carriers such as an aqueous or nonaqueous solvent. Examples of solvents which may be used are distilled water for injection, physiological saline solution, Ringer's solution, plant oil, synthetic fatty acid glycerides, higher fatty acid esters, propylene glycol, etc.

In the case of inhalations or aerosol preparations, at least one compound of the present invention in the form of a liquid or minute powder can be filled up in an aerosol container with a gas or liquid spraying agent, and if desired, with conventional adjuvants such as one or more pharmaceutically acceptable humidifying agents or dispersing agents. They can also be used as pharmaceuticals for a non-pressurized preparation such as in a nebulizer or an atomizer.

It is also possible, depending upon the type of the disease, to prepare pharmaceutical preparations other than the above-mentioned ones which are suitable for therapy depending upon the state of the patient. Exemplary of other pharmaceutical preparations are syrups, collyriums, medicines for external use (e.g. ointments, gels, poultices), etc.

The preferred dosage of the compound of the present invention varies depending upon the subject to be administered (age, body weight, symptoms, etc. of the patient), form of the preparation, method for the administration, term for the administration, etc. To achieve the desired result, the compound may be usually administered by the oral route with a daily dose of 0.1–100 mg per day, preferably 1–50 mg per day, to common adults.

In the case of a parenteral administration such as by injection, the preferred dosage, may be from $\frac{1}{3}$ to $\frac{1}{10}$ of the above-mentioned oral dosages because of the effects of absorption, etc. in the oral route.

The present invention is further illustrated by the following non-limiting examples wherein all parts, percentages and ratios are by weight, all temperatures are in ° C., and all reactions are conducted at about atmospheric pressure unless indicated to the contrary. In the following examples, melting point was measured by placing the sample in a capillary made of glass using a melting point measuring device (type MP-21 manufactured by Yamato). Mass spectrum was measured by ionizing by means of an SIMS method using a device (type M-80B manufactured by Hitachi). Measurement of nuclear magnetic resonance (NMR) was conducted by dissolving the sample in DMSO-$d_6$ (containing 0.05% of tetramethylsilane as an internal standard) using a device (ARX-500 manufactured by Brucker). Elementary analysis was conducted using a CHN corder MT-5 manufactured by Yanako:

COMPARATIVE EXAMPLE 1

In this example, two control compounds are produced where the substituent in the 2position has only one or two carbon atoms, 9-(β-D-arabinofuranosyl)-2-methyladenine (control compound A) and 9-(β-D-arabinofuranosyl)-2-ethyladenine (control compound B), respectively:

A. Synthesis of 9-(β-D-arabinofuranosyl)-2-methyladenine [control compound A]

AICN arabinoside (1 g) and acetonitrile (2 mL) were dissolved in 50 mL of methanol saturated with ammonia of 0° C., placed in an autoclave and heated at 140° C. for 16 hours. After completion of the reaction, the solvent was evaporated and the residue was separated and purified by a silica gel column and recrystallized from distilled water to give a control compound A (745 mg) as yellow needles.

M.P.: 247–249° C.

Mass: 282(MH$^+$).

$^1$H-NMR: 2.39(1H,s), 3.64(2H,m), 3.76(1H,m), 4.12(2H, m), 5.13(1H,t,j=4.9), 5.51(1H,d,j=4.4), 5.60(1H,d,j=4.9), 6.22(1H,d,j=4.9), 7.10(2H,s), 8.09(1H,s).

B. Synthesis of 9-(β-D-arabinofuranosyl)-2-ethyladenine [control compound B]

In the above-mentioned reaction, the nitrile corresponding to the starting acetonitrile were used and the same reaction as in Comparative Example 1A was conducted to give a control compound B:

9-(β-D-arabinofuranosyl)-2-ethyladenine [control compound B]

M.P.: 242–243° C.

Mass: 296(MH$^+$).

$^1$H-NMR: 1.23(3H,t,j=7.6), 2.65(2H,q,j=7.6), 3.65(2H, m), 3.76(1 5.10(1H,t,j=6.0), 5.52(1H,d,j=3.8), 5.62(1H,d,j= 5.5), 6.24(1H,d,j=4.9), 7.09(2H,s), 8.08(1H,s).

COMPARATIVE EXAMPLE 2

In this example, a control compound is produced which is not substituted in the 2-position, but is substituted in the six position with a methylamino group, 6-methylamino-9-(β-Darabinofuranosyl)purine [control compound C]:

Synthesis of 6-methylamino-9-(β-D-arabinofuranosyl) purine [control compound C].

N$^6$-Methyladenosine (1 g) and 1.35 g of 1,3-dichlorotetraisopropyldisiloxane were dissolved in 20 mL of pyridine and stirred at room temperature for 2 hours. After completion of the reaction, the solvent was evaporated and the residue was separated and purified by a silica gel column and recrystallized from ethyl acetate to give 1.9 g of 6-methylamino-9-[3,5-O-(tetraisopropyldisiloxan-1,3-diyl)-β-D-ribofuranosyl]purine. This compound (100 mg) was dissolved in a mixture of 4 mL of acetic anhydride and 10 mL of dimethyl sulfoxide (DMSO) and stirred at room temperature for 16 hours. After the reaction, the solvent was evaporated followed by dissolving in 20 mL of L-(-)-5,6,7, 8-tetrahydrofolic acid (THF). To this solution were added 50 mg of sodium borohydride followed by stirring for 30 minutes. Then 2 mL of ethanol were added followed by stirring for 1 hour more. After a small amount of acetone was added to the reaction solution, the mixture was evaporated to dryness and 1 mL of a solution of 1 M tetrabutylammonium fluoride in THF was added to the residue. The solvent was evaporated and the residue was separated and purified by a silica gel column and recrystallized from distilled water to give a control compound C (34 mg) as colorless needles.

M.P.: 194–198° C.

$^1$H-NMR: 2.95(3H,s), 3.65(2H,m), 3.78(1H,m), 4.13(2H, m), 5.09(1H,t,j=4.9), 5.51 (1H,d,j=4.4), 5.61(1H,d,j=4.9), 6.26(1H,d,j=4.4), 7.70(1H,s), 8.17(1H,s), 8.22(1H,s).

EXAMPLE 1

In the reaction of Comparative Example 2, the adenosine derivatives corresponding to the starting N$^6$-methyladenosine were used and the same reaction as in Comparative Example 2 was conducted to give compounds 1 and 2:

6-methylamino-9-(β-D-arabinofuranosyl)-2-butylpurine [compound 1]

M.P.: 165–166° C.

Mass: 319(MH$^+$).

Elementary analysis: calculated as $C_{15}H_{23}N_5O_4 \cdot 0.2H_2O$.

Theoretical: (C, 52.98; H, 6.91; N, 20.59); Found: (C, 52.98; H, 6.74; N, 20.76).

$^1$H-NMR: 0.91(3H,tj=7.6), 1.35(2H,hex,j=7.6), 1.71(2H, qui,j=7.6), 2.67(2H,t,j=7.6), 2.95(3H,s), 3.64(2H,m), 3.76 (1H,m), 4.13(2H,m), 5.09(1H,tj=5.5), 5.51(1H,d,j=4.4), 5.61(1H,d,j=5.5), 6.24(1H,d,j=4.4), 7.50(1H,s), 8.06(1H,s).

6-methylamino-9-(β-D-arabinofuranosyl)-2-(1-butyne-1-yl) purine [compound 2]

M.P.: 243–246° C.

Mass: 334(MH$^+$).

Elementary analysis: calculated as $C_{14}H_{22}N_6O_4$.

Theoretical: (C, 49.70; H, 6.55; N, 24.84); Found: (C, 45.28; H, 6.13; N, 21.29_j.

$^1$H-NMR: 1.17(3H,t,j=7.6), 2.42(2H,q,j=7.6), 2.92(3H,s), 3.65(2H,m), 3.78(1H,m), 4.12(2H,m), 5.07(1H,t,j=5.5), 5,51(1H,d,j=5.5), 5.60(1H,d,j=5.5), 6.21(1H,dj=4.9), 7.76 (1H,s), 8.20(1H,s)

EXAMPLE 2

Synthesis of 9-(β-D-arabinofuranosyl)-2-(1-butyne-1-yl) adenine [compound 3]

(1) To 5 g of 2-iodoadenosine were added 50 mL of pyridine, then 4.4 g of dichlorotetraisopropyldisiloxane (TIPDSCl$_2$) were added with ice cooling and stirring and the mixture was stirred at room temperature for 1 hour. After the reaction, the solvent of the reaction solution was evaporated and the residue was recrystallized from methanol to give 2-iodo-9-[3,5-O-(tetraisopropyldisiloxan-1,3-diyl)-p-D-ribofuranosyl]-adenine (6.3 g) as colorless needles.

M.P.: 140–142° C.

$^1$H-NMR: 1.05(28H,m), 3.93(1H,dd,j=2.7, 12.5), 3.98 (1H,m), 4.03(1H,dd,j=3.8, 12.5), 4.54(1H,m), 4.60(1H,dd, j=5.5, 8.7), 5.16(1H,m), 5.80(1H,s), 7.74(2H,s), 8.13(1H,s)

(2) 2-Iodo-9-[3,5-O-(tetraisopropyldisiloxan-1,3-diyl)-β-D-ribofuranosyl]adenine (970 mg) obtained in the above paragraph (1) was dissolved in 20 mL of pyridine, then 400 µL of trifluoromethanesulfonic acid chloride, 400 mg of 4-dimethylaminopyridine and 400 µL of triethylamine were added thereto with ice cooling and the mixture was stirred for 30 minutes. The reaction solution was concentrated to dryness and the residue was dissolved in 0.1 N hydrochloric acid and extracted with chloroform. The extract was separated and purified by a silica gel column. The purified extract was recrystallized from ethyl acetate to give 2-iodo-9-[2-O-trifuryl-3,5-(tetraisopropyldisiloxan-1,3-diyl)-β-D-arabinofuranosyl]-adenine (910 mg) as colorless needles.

$^1$H-NMR: 1.05(28H,m), 4.00(2H,m), 4.09(1H,m), 5.05 (1H,dd,j=4.9, 8.7), 6.04(1H,d,j=4.9), 6.41(1H,s), 7.82(2H, s), 8.14(1H,s) (3) 2-Iodo-9-[2-O-trifuryl-3,5-(tetraisopropyl-disiloxan-1,3-diyl)-β-D-arabinofuranosyl] adenine (900 mg) prepared in the above paragraph (2) was dissolved in 25 mL of N,N-dimethylformamide (DMF), 500 mg of anhydrous sodium acetate were added and the mixture was stirred at room temperature for 4 days. After completion of the reaction, the solvent was evaporated and the residue was separated and purified by a silica gel column. The purified product was recrystallized from ethyl acetate to give 2-iodo-9-[2-O-acetyl-3,5-O-(tetraisopropyldisiloxan-1,3-diyl)-β-D-arabinofuranosyl]adenine (633 mg) as colorless needles.

$^1$H-NMR: 1.05(28H,m), 1.67(3H,s), 3.96(2H,m), 4.16 (1H,m), 4.87(1H,t,j=7.1), 5.57(1H,t,j=7.1), 6.34(1H,dj=7.1), 7.76(2H,s), 8.00(1H,s).

(4) 2-Iodo-9-[2-O-acetyl-3,5-O-(tetraisopropyl-disiloxan-1,3-diyl)-β-D-arabinofuranosyl]adenine (25 g) prepared in the above paragraph (3) was dissolved in 300 mL of THF and a solution of 1M tetrabutylammonium fluoride in 110 mL of THF was added thereto. The mixture was stirred at room temperature for 30 minutes, 100 mL of aqueous ammonia were added thereto and the mixture was stirred at room temperature for 2 hours more. After evaporation of the solvent, deionized water was added to the residue, the mixture was allowed to stand at 4° C. and the separated crystals were collected. They were recrystallized from distilled water to give 2-iodo-9-(β-D-arabinofuranosyl)adenine (13.38 g) as colorless needles.

$^1$H-NMR: 3.65(2H,m), 3.76(1H,m), 4.11(1H,m), 4.15 (1H,m), 5.03(1H,t,j=5.5), 5.52(1H,d,j=4.9), 5.62(1H,d,j= 4.9), 6.14(1H,d,j=5.4), 7.65(2H,s), 8.11(1H,s)

(5) 2-Iodo-9-(β-D-arabinofuranosyl)adenine (2.5 g) obtained in the above paragraph (4), 100 mg of bis (triphenylphosphine)-palladium (II) chloride, 200 mg of cupric iodide and 450 mg of butyne were dissolved in a mixture of 75 mL of DMSO and 25 mL of triethylamine and the reaction was carried out at 80° C. for 2 hours. The solvent was evaporated from the reaction solution and the residue was separated and purified by a silica gel column and recrystallized from distilled water to give compound 3 (1.75 g) as colorless needles:

9-(β-D-arabinofuranosyl)-2-(1-butyne-1-yl)adenine [compound 3]

M.P.: 273–279° C.

Mass: 320(MH$^+$).

Elementary analysis: calculated as $C_{14}H_{17}N_5O_4$.

Theoretical: (C, 52.66; H, 5.37; N, 21.93); Found: (C, 52.39; H, 5.28; N, 21.68).

$^1$H-NMR: 1.1$^6$($^3$H,t,j=7.6), 2.40(2H,q,j=7.6), 3.65(2H,m), 3.78(1H,m), 4.12(2H,m), 5.06(1H,t,j=5.5), 5.51(1H,d,j= 4.4), 5.60(1H,d,j=5.4), 6.21(1H,d,j=4.9), 7.31(2H,s), 8.21 (1H,s).

EXAMPLE 3

Other 2-alkynl adenine derivatives of the present invention were produced as in Example 2 except, in paragraph 5 of the above-mentioned Example 2 reaction, a different alkyne corresponding to the starting butyne was used and the same reaction as in Example 2 was conducted to give compounds 4, 5 and 6:

9-(β-D-arabinofuranosyl)-2-(1-hexyne-1-yl)adenine [compound 4]

$^1$H-NMR: 0.91 (3H,t,j=7.1), 1.43(2H,hex,j=7.1), 1.53 (2H,qui,j=7.1), 2.40(2H,t,j=7.1), 3.65(2H,m), 3.78(1H,m), 4.12(2H,m), 5.06(1H,t,j=4.9), 5.51(1H,d,j=4.9), 5.60(1H,d, j=5.5), 6.20(1H,d,j=5.5), 7.41(2H,s), 9.00(1H,s).

9-(β-D-arabinofuranosyl)-2-(1-octyne-1-yl)adenine [compound 5]

$^1$H-NMR: 0.88(3H,t,j=7.1), 1.29(4H,m), 1.41(2H,m), 1.54(2H,qui,j=7.1), 2.40(2H,t,j=7.1), 3.65(2H,m), 3.78(1H, m), 4.12(2H,m), 5.06(1H,t,j=5.5), 5.51 (1H,d,j=4.4), 5.60 (1H,d,j=4.9), 6.20(1H,d,j=4.9), 7.31(2H,s), 8.21(2H,s).

9-(β-D-arabinofuranosyl)-2-(1-dodectyne-1-yl)adenine [compound 6]

$^1$H-NMR: 0.85($^3$H,t,j=7.1), 1.26(16H,m), 1.40(2H,m), 1.5$^3$($^2$H,qui,j=7.1), 2.39(2H,t,j=7.1), 3.65(2H,m), 3.77(1H, m), 4.12(2H,m), 5.07(1H,t,j=5.5), 5.51(1H,d,j=4.4), 5.60 (1H,d,j=5.5), 6.20(1H,d,j=4.9), 7.32(2H,s), 8.21(1H,s).

EXAMPLE 4

Synthesis of 9-(β-D-arabinofiranosyl)-2-butyladenine [compound 7]

9-(β-D-arabinofuranosyl)-2-(1-butyne-1-yl)adenine [compound 3] in an amount of 2 g was dissolved in 30 mL of 50% methanol, 10 mg of 10% palladium carbon were added thereto and the mixture was stirred at room temperature for 16 hours. The catalyst was filtered off, the filtrate was concentrated and the crystals separated out therefrom were collected. They were recrystallized from distilled water to give a compound 7 (1.95 g) as colorless needles: ps 9-(β-D-arabinofuranosyl)-2-butyladenine [compound 7]

M.P.: 162–163° C.

Mass: 324(MH+).

Elementary analysis: calculated as $C_{14}H_{21}N_5O_4 \cdot 0.1H_2O$.

Theoretical: (C, 51.72; H, 6.57; N, 21.54); Found: (C, 51.63; H, 6.49; N, 21.54)

$^1$H-NMR: 0.90(3H,t,j=7.6), 1.33(2H,hex,j=7.6), 1.69(2H, qui,j=7.6), 2.63(2H,t,j=7.6), 3.65(2H,m), 3.77(1H,m), 4.13 (2H,m), 5.09(1H,tj=6.6), 5.50(1H,d,j=4.4), 5.61(1H,d,j= 5.5), 6.23(1H,d,j=4.4), 7.06(2H,s), 8.07(1H,s).

EXAMPLE 5

Other 2-alkyl adenine derivatives of the present invention were produced as in Example 4 except instead of using 9-(β-D-arabinofuranosyl)-2-(1-butyne-1-yl)adenine

[compound 3] as a starting compound, 9-(β-D-arabinofuranosyl)-2-(1-hexyne-1-yl)adenine [compound 4], 9-(β-D-arabinofuranosyl)-2-(1-octyne-1-yl)adenine [compound 5] or 9-(β-D-arabinofuranosyl)-2-(1-dodectyne-1-yl)adenine [compound 6] corresponding to the starting compound (compound 3) were used and the same reaction as in Example 4 was conducted to give compounds 8, 9 and 10, respectively:

9-(β-D-arabinofuranosyl)-2-hexyladenine [compound 8].
M.P.: 98–103° C.
Mass: 352(MH$^+$).
Elementary analysis: calculated as $C_{16}H_{25}N_5O_4 \cdot 0.25H_2O$.
Theoretical: (C, 54.00; H, 7.22; N, 19.68); Found: (C, 53.87; H, 7.04; N, 19.64).
$^1$H-NMR: 0.86(3H,t,j=7.1), 1.28(6H,m), 1.69(2H,qui,j=7.1), 2.62(2H,t,j=7.1), 3.64(2H,m), 3.76(1H,m), 4.12(2H,m), 5.09(1H,t,j=5.5), 5.51(1H,d,j=4.4), 5.62(1H,d,j=5.5), 6.23(1H,d,j=4.4), 7.07(2H,s), 8.07(1H,s).

9-(β-D-arabinofuranosyl)-2-octyladenine [compound 9].
M.P.: 65–68° C.
Mass: 380(MH$^+$).
Elementary analysis: calculated as $C_{18}H_{29}N_5O_4 \cdot 0.5H_2O$.
Theoretical: (C, 55.65; H, 7.78; N, 18.03); Found: (C, 55.59; H, 7.63; N, 18.19).
$^1$H-NMR: 0.86(3H,t,j=7.1), 1.27(10H,m), 1.69(2H,qui,j=7.1), 2.62(2H,t,j=7.1), 3.64(2H,m), 3.77(1H,m), 4.13(2H,m), 5.09(1H,t,j=4.9), 5.50(1H,d,j=4.4), 5.61(1H,d,j=5.5), 6.23(1H,d,j=4.9), 7.06(2H,s), 8.07(1H,s).

9-(β-D-arabinofuranosyl)-2-dodecyladenine [compound 10].
M.P.: 67–74° C.
Mass: 436(MH$^+$).
Elementary analysis: calculated as $C_{22}H_{37}N_5O_4 \cdot 0.45H2O$.
Theoretical: (C, 59.56; H, 8.61; N, 15.78); Found: (59.49; H, 8.54; N, 15.85).
$^1$H-NMR: 0.85(3H,t,j=7.1), 1.25(18H,m), 1.67(2H,m), 2.61 (2H,t,j=7.1), 3.65(2H,m), 3.76(1H,m), 4.13(2H,m), 5.10(1H,tj=5.5), 5.51(1H,d,j=4.9), 5.61(1H,d,j=5.5), 6.23 (1H,d,j=4.9), 7.07(2H,s), 8.07(2H,s).

EXAMPLE 6

Measurement of Antiviral Activity

Figure 2:
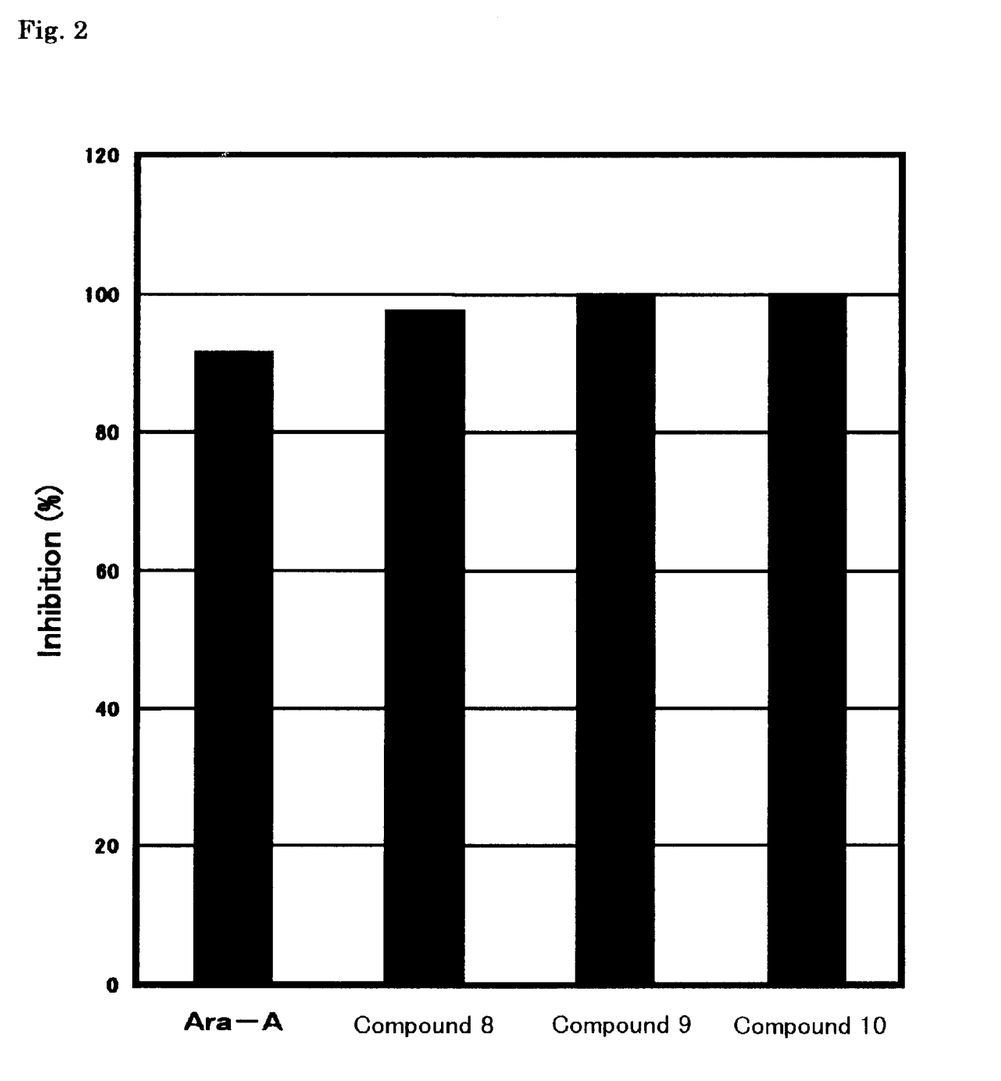
FIG. 2 is also an example of results showing the inhibitory activity of the compounds of the present invention against herpes zoster virus.

Antiviral activity of the compounds of the present invention was investigated by the following pharmacological experiments:

As a test for efficacy of antiviral activity, antiviral activity to shingles herpes virus was measured. Cell-free aricella-zoster virus (VZV) (Kawaguchi strain) was diluted and the resulting solution was layered on HEL cells of a 100% confluent. The layered product was placed in a $CO_2$ incubator of 37° C., shaken every 15 minutes and infected for one hour. The virus solution was removed by suction, then DMEM containing 5% of FCS and a compound of the present invention, a control compound or Ara-A (positive control) was added thereto and the mixture was incubated for one week. The incubated mixture was fixed by formalin, dyed with Crystal Violet and numbers of plaques were measured. The inhibiting rate to shingles virus was determined from the plaque numbers of the control. The results for antiviral activity towards shingles virus is shown in FIG. 1 and FIG. 2. The compounds of the present invention had a substantial, sufficient antiviral activity to shingles virus.

Further, the antiviral activity of the compounds of the present invention to herpes simplex virus type 1 and type 2 was measured by the same manner as mentioned above and, as a result, the compounds of the present invention had a substantial, sufficient antiviral activity to herpes simplex virus type 1 and type 2 as well.

EXAMPLE 7

Measurement of Stability to ADA

Stability of the compounds of the present invention to ADA was investigated by the following biochemical experiments:

An enzymatic reaction was carried out to test stability of the compounds to ADA. Thus, 200 μL (final concentration: 0.1 mM) of a 1 mM solution of a compound of the present invention, a control compound or Ara-A (control), 1.5 mL of a 0.1 M phosphate buffer (pH 7.5; final concentration: 75 mM) and 300 μL of a 200 units/mL enzyme solution (final concentration: units/mL) were placed in a UV cell and the decrease in ultraviolet absorption at 265 nm with a lapse of time was measured by an ultraviolet absorption meter. The enzymatic reaction was carried out at 25° C. As the enzymatic reaction proceeded, an ultraviolet absorption at 265 nm decreased and said rate of decrease in ultraviolet absorption was expressed as a relative enzymatic reaction rate. An example of the results is shown in FIG. 4. The control compound 6methylamino-9-(β-D-arabinofuranosyl)purine [control compound C] had insufficient resistance to metabolism by ADA while all of the compounds of the present invention were very stable to metabolism by ADA.

As shown in FIG. 1 and FIG. 2, a sufficient antiviral action is not achieved even when a lower alkyl group such as methyl or ethyl is introduced into the 2-position of Ara-A (control compounds A and B). However, the compounds of the present invention where an aliphatic hydrocarbon group having 4 or more carbons is introduced into the 2-position of Ara-A showed antiviral action unexpectedly higher than that of control compounds A and B and at least substantially as good as the antiviral activity of Ara-A.

Figure 3:
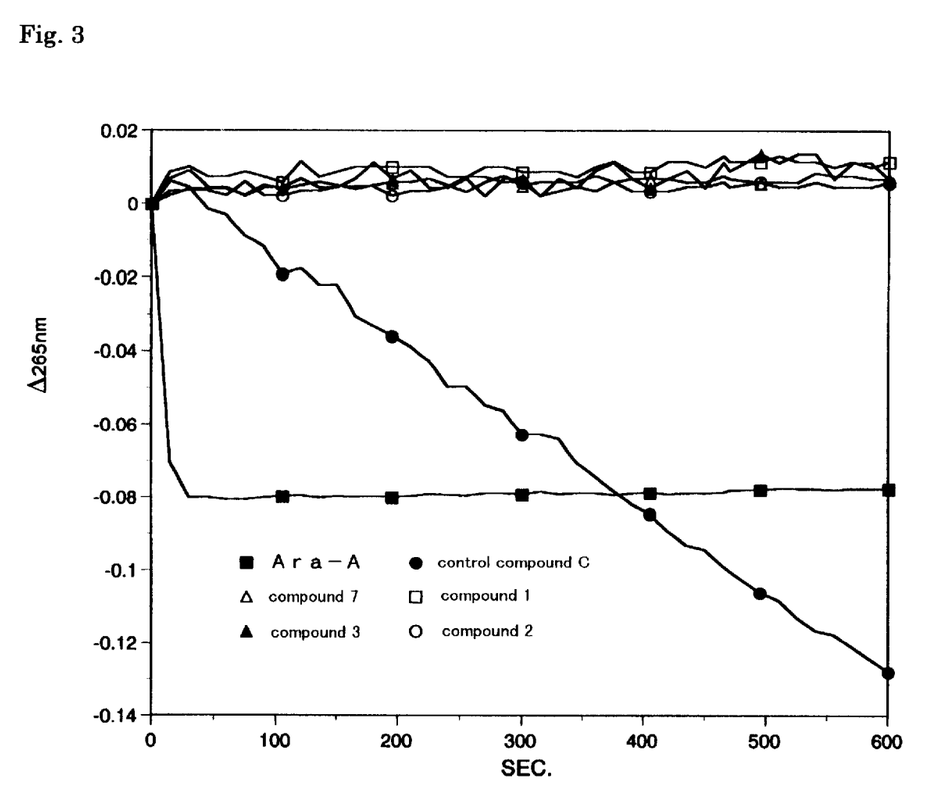
FIG. 3 is an example of result showing resistance of compounds of the present invention to metabolism by adenosinedeaminase (ADA).

In addition, as shown in FIG. 3, the compound where a substituent is introduced into the 6-position of the base portion of Ara-A (control compound C) was metabolized by ADA. Further, although not shown in the drawing, compounds where a methyl or ethyl group is introduced into the 2-position of Ara-A (control compounds A and B) did not show a favorable resistance to ADA.

On the contrary, regarding the compounds of the present invention where an aliphatic hydrocarbon group having 4 or more carbons is introduced into the 2-position of Ara-A, the decomposition was unexpectedly completely inhibited and had a substantial, sufficient resistance to metabolism by ADA. Therefore, even though effective oral administration of the known, control compounds (Ara-A, and control compounds A, B, and C) has been impossible, the compounds of the present invention are capable of unexpectedly effective oral administration.

As such, the compounds of the present invention are Ara-A derivatives having a resistance to metabolism by ADA and having a sufficient antiviral action whereby the problems exhibited by the control compounds (Ara-A, and control compounds A, B, and C) have been solved. The compounds of the present invention are useful as therapeutic or preventive agents for diseases infected by DNA virus such as herpes simplex virus (HSV), herpes zoster virus, cytomegalovirus (CMV), adenovirus, hepatitis virus or vaccinia virus. As compared with Ara-A, they not only show good behavior in blood with an excellent sustaining property but also are capable of being orally administered whereby their usefulness is very high.

We claim:

1. A compound which is a 2-substituted arabinosyladenine derivative represented by the formula (I) or a pharmaceutically acceptable salt or hydrate thereof:

[I]

wherein Z is alkyl having at least 4 carbon atoms, $C_{2-12}$ alkenyl or $C_{2-12}$ alkynyl and R is hydrogen or $C_{1-4}$ lower alkyl.

2. A compound as claimed in claim 1 wherein Z is alkyl having more than 4 carbon atoms, alkenyl having more than 4 carbon atoms or alkynyl having more than 4 carbon atoms.

3. A compound as claimed in claim 1 wherein Z is alkyl or alkynyl.

4. A compound as claimed in claim 2 wherein Z is alkyl or alkynyl.

5. A compound as claimed in claim 1 wherein Z is alkyl.

6. A compound as claimed in claim 5 wherein Z is alkyl having 4 to 12 carbon atoms.

7. A compound as claimed in claim 6 wherein R is hydrogen.

8. A compound as claimed in claim 6 wherein R is alkyl.

9. A compound as claimed in claim 1 wherein Z is alkynyl.

10. A compound as claimed in claim 9 wherein Z is alkynyl having 4 to 12 carbon atoms.

11. A compound as claimed in claim 10 wherein R is hydrogen.

12. A compound as claimed in claim 10 wherein R is alkyl.

13. A compound as claimed in claim 4 wherein R is hydrogen.

14. An antiviral agent containing a compound according to claim 1 as an effective component.

15. An antiviral agent as claimed in claim 14 which is a preparation for oral administration.

16. An antiviral agent as claimed in claim 14 wherein Z is alkyl having 4 to 12 carbon atoms and R is hydrogen.

17. A pharmaceutical composition comprising a pharmaceutically effective amount of at least one compound according to claim 1 and a pharmaceutically acceptable carrier.

18. A pharmaceutical composition as claimed in claim 17 which is orally administratable and wherein Z is alkyl having 4 to 12 carbon atoms and R is hydrogen.

19. A method for the treatment of a disease caused by a DNA virus comprising orally administering to a patient in need of such treatment a pharmaceutically effective amount of at least one compound according to claim 1.

* * * * *